United States Patent [19]

Cormier et al.

[11] Patent Number: 5,571,396

[45] Date of Patent: Nov. 5, 1996

[54] FLUID ANALYSIS SYSTEM AND SENSING ELECTRODE, ELECTRODE ASSEMBLY, AND SENSING MODULE COMPONENTS

[75] Inventors: Alan D. Cormier, Newburyport, Mass.; Melvin S. Weinberg, Nashua; Ronald L. Jones, Newton, both of N.H.; Janet D. Vitiello, Bedford, Mass.

[73] Assignee: Dade International Inc., Deerfield, Ill.

[21] Appl. No.: 90,581

[22] Filed: Jul. 12, 1993

[51] Int. Cl.⁶ .................. G01N 27/403; G01N 27/414
[52] U.S. Cl. .................. 204/418; 204/409; 422/81; 422/82; 422/82.01; 422/82.02; 422/82.03; 422/82.04
[58] Field of Search .................. 204/409, 412, 204/415, 416, 418, 435; 422/81, 82, 82.01, 82.02, 82.03, 82.04

[56] References Cited

U.S. PATENT DOCUMENTS

| | | | |
|---|---|---|---|
| 3,700,576 | 10/1972 | Block et al. | 204/418 |
| 3,884,640 | 5/1975 | Lock et al. | 422/82.04 X |
| 4,017,374 | 4/1977 | Aas et al. | 204/409 |
| 4,160,714 | 7/1979 | Andersen et al. | 204/411 |
| 4,283,262 | 8/1981 | Cormier et al. | 204/412 X |
| 4,293,307 | 10/1981 | Simpson et al. | 23/230 B |
| 4,299,728 | 11/1981 | Cormier et al. | 252/408 |
| 4,353,789 | 10/1982 | Kashkai | 204/409 |
| 4,361,539 | 11/1982 | Weinberg et al. | 422/82.02 |
| 4,361,540 | 11/1982 | Weinberg et al. | 422/82.02 |
| 4,366,038 | 12/1982 | Kearney et al. | 204/195 M |
| 4,369,127 | 1/1983 | Cormier et al. | 436/111 |
| 4,399,362 | 8/1983 | Cormier et al. | 250/430 |
| 4,410,631 | 10/1983 | Czaban et al. | 436/8 |
| 4,443,407 | 4/1984 | Weinberg et al. | 422/68 |
| 4,531,088 | 7/1985 | Czaban et al. | 204/411 |
| 4,604,166 | 8/1986 | Wienberg et al. | 204/1 T |
| 4,627,893 | 12/1986 | Cormier et al. | 204/409 X |
| 4,640,821 | 2/1987 | Mody et al. | 422/82 X |
| 4,680,270 | 7/1987 | Mitsumaki et al. | 436/52 |
| 4,786,372 | 11/1988 | Jones et al. | 204/1 T |
| 4,902,399 | 2/1990 | Durley, III et al. | 204/409 |
| 4,929,426 | 5/1990 | Bodai et al. | 422/82.04 X |
| 4,935,117 | 6/1990 | Uematsu et al. | |
| 4,946,651 | 8/1990 | Liston et al. | 422/102 |
| 4,964,971 | 10/1990 | Riemann | 204/409 X |
| 5,019,238 | 5/1991 | Cormier et al. | 204/409 |
| 5,078,854 | 1/1992 | Burgess et al. | 204/403 |
| 5,112,454 | 5/1992 | Tanaka et al. | 204/153.1 |
| 5,145,565 | 9/1992 | Kater et al. | 204/153.1 |
| 5,164,067 | 11/1992 | Marsoner et al. | 204/416 |
| 5,192,416 | 3/1993 | Wang et al. | 204/409 |
| 5,194,133 | 3/1993 | Clark et al. | 204/299 R |
| 5,200,052 | 4/1993 | Ishibashi | 204/409 |
| 5,221,457 | 6/1993 | North et al. | 204/416 |

FOREIGN PATENT DOCUMENTS

| | | |
|---|---|---|
| 514575A1 | 11/1992 | European Pat. Off. . |
| 544237A1 | 6/1993 | European Pat. Off. . |
| 2021318 | 1/1971 | Germany . |
| 132210 | 9/1978 | Germany . |
| 4-084750A | 3/1992 | Japan . |
| 4-143650A | 5/1992 | Japan . |
| WO93/06483 | 4/1993 | WIPO . |

OTHER PUBLICATIONS

R. Virtanen *Anal. Chem. Symp. Ser.* 1981, 8, 375–385.
J. G. Schindler et al. *Biomed. Tech.* 1991, 36, 271–284.
A. K. Covington et al. *J. Chem. Soc. Faraday Trans.* 1993, 89, 369–376.
W. Simon et al. *Agew. Chem. Internat. Edit.* 1970, 9, 445–455.
H. F. Osswald et al. *Clin. Chem.* 1979, 25, 39–43.
R. Virtanen *Chem. Abstr.* 1982, 96, 228105f.
U. Oesch et al. *Clin. Chem.* 1986, 32, 1448–1459.
E. Metzger et al. *Anal. Chem.* 1987, 59, 1600–1603.
A. K. Covington et al. *Chem. Abstr.* 1993, 118, 164552n.

Primary Examiner—Arlen Soderquist
Attorney, Agent, or Firm—Linda M. Buckley

[57] ABSTRACT

The present invention provides sensing electrodes and electrode assemblies for use in measuring the activity of ions in a fluid sample; measuring blocks which include a sensing module housing such sensing electrodes and a reference electrode; and a fluid analysis system which includes such measuring blocks.

17 Claims, 10 Drawing Sheets

FLUID ANALYSIS SYSTEM AND SENSING ELECTRODE, ELECTRODE ASSEMBLY, AND SENSING MODULE COMPONENTS

BACKGROUND OF THE INVENTION

This invention relates to apparati for and methods of analyzing fluid samples and has particular application in the analysis of parameters of biological fluids, such as blood and serum.

Systems for analyzing the ion level of a fluid sample by use of ion selective electrodes are known in the art. Such systems typically include an analyzer instrument which contains electrical circuitry for analyzing the ion levels of the fluid sample. The electrical circuitry is adapted to receive information from measuring units which include the ion selective electrodes. Conventional electronics, pumping and flow meters and the like are interconnected with such measuring units.

Measuring units have been used in various electrochemical measuring apparatus. U.S. Pat. No. 4,160,714 describes a single unit measuring chamber used for pH values, gas values and other types are known for use in measuring various analytes including metal ions in body fluids such as blood.

It is known to use reference electrodes and measure electromotive force between a reference electrode and an electrode mounted beneath a membrane over which a fluid is passed to determine the ionic content of the fluid. Ions such as potassium, sodium and others are customarily tested in medical laboratories by such equipment. For example, U.S. Pat. Nos. 4,627,893 and 5,019,238 disclose a testing module having units which can be arranged seriatim to provide narrow through passageways linked to each other for quantitative determination of analytes passing through the units as by electrical testing with electrodes.

A module multi-channel automated medical analyzer device characterized by use of an ion selective electrode is disclosed in U.S. Pat. No. 4,946,651. Other systems for analyzing ion levels in fluids are disclosed, for example, in U.S. Pat. No. 4,293,307; U.S. Pat. No. 4,221,457; and U.S. Pat. No. 4,946,651.

SUMMARY OF THE INVENTION

This invention provides means and methods for rapidly, efficiently and quantitatively determining ionic concentration of various ions in fluids, as for example the blood.

This invention also provides a novel measuring block which can be used for rapid quantitative and efficient measurement with high accuracy of ionic components of extremely small volumes of body fluids and in a manner which minimizes contamination of the sample to a great extent.

Measuring blocks are provided in accordance with the preceding objects wherein the measuring block is removably engageable to an analyzer instrument containing electrical circuitry for receiving electronic signals from electrodes in the measuring block and wherein the measuring block comprises (i) a sensing module containing at least one novel ion selective electrode (sensing electrode), and (ii) a reference electrode, in electrical communication through a liquid junction. In one preferred embodiment, the sensing module and reference electrode are removably engageable for ease of replacement. Both the sensing electrodes and the entire sensing module, as well as the reference electrode, are easily replaced, thereby allowing for replacement of the components of the measuring blocks of the present invention in a rapid and efficient manner.

In preferred embodiments of the present invention, wherein the measuring block is adapted to connect to an analyzer instrument, these connections are made with conventional signal processing, communications and connector boards, mounting bracket for the measuring block and so forth. Once mounted and in communication with the electrical circuitry of an analyzer, the measuring block is integrated with various pumps, calibration liquids, wash stations and so forth, all of which are conventionally used in such analyzer instruments.

The measuring block is adapted to be removably engaged with the analyzer and includes electrical contacts for communication with electrical contacts in the analyzer instrument. The electrical contacts in the analyzer instrument which correspond to the electrical contacts of the measuring module, particularly those of the sensing electrodes, are, in preferred embodiments, resiliently mounted. The resilient means that allow movement of the electrical contacts may be springs or other means known in the art.

This invention also provides means and methods for introduction of sample, as well as calibrating and cleaning solutions, to selected portions of the measuring block rapidly and efficiently, minimizing contaminating these solutions with reference electrode filing solution or other sources of contaminants.

One preferred sensing module of the present invention comprises at least one sensing electrode in accordance with the present invention, when the sensing electrode is arranged to provide for at least one in-line ionic test to quantitatively determine an ion in a sample passed through the sensing module rapidly and efficiently. In another embodiment, the sensing module comprises a plurality of such sensing electrodes, arranged to provide for a plurality of in-line ionic tests.

The sensing module is optionally provided with one or more optical sensors and temperature detectors. In some such embodiments, optical ports are provided in the flow path below the inlet port and sample well and after the reference junction point for connection to optical sensors. The sensing module is preferably made of transparent material so that fluid sample in the flow path may be visually observed.

The sensing module further comprises one or more electrode holders for removably receiving a sensing electrode, one or more inlet and outlet ports connected by a flow path for the passage of liquids, e.g., a sample to be measured, calibrants, wash liquids and so forth.

Each electrode holder is in communication with the flow path by means of an opening between the flow path and the electrode holder. The electrode holders are preferably arranged in line on one side of the sensing module to allow easy replacement of the electrodes and engagement of electrical contacts on a circuit board. In yet other embodiments, electrode holders are placed on alternate or multiple sides of the sensing module to minimize the size thereof and, thus, the size of the sample required.

One particularly preferred sensing module for use in accordance with this invention comprises:

(i) a flow-through cell having at least one inlet port and at least one outlet port;

(ii) at least one flow path in the cell for the sample, the flow path being in communication with the inlet and outlet ports and having at least two openings between the ports, a first opening for communicating with a sensing electrode and a second opening for communicating with a reference electrode;

(iii) at least one hollow cylindrical member in the cell adapted to receive a sensing electrode and terminating at one end in a hemispherical member having an opening in communication with the flow path for the sample and at the opposite end in an opening to receive the electrode; and (iv) at least one sensing electrode in accordance with the present invention.

In particularly preferred embodiments of this invention, to facilitate servicing and eliminate wiring harnesses, all electrical connections to the analyzer are made by electrical contacts resiliently mounted on the analyzer such as, "POGO™" type pin connections[1] (spring loaded contact pins). This includes, where present, sensing electrodes, reference electrodes, optical sensors, temperature measurement contacts and ground.

[1] POGO is a trademark of AUGAT, 425 John Dietsch Boulevard, Attleborro Falls, Mass. 02763

To minimize clogging and bubble traps, in preferred embodiments the flow path from inlet port past the sensing electrodes is substantially straight, with no seals other than the seal provided by the tips of the electrodes when they are positioned in the electrode holders disposed in the sensing module. The seal is made by compliant ion selective membrane material disposed on the tips of the novel electrodes of the present invention which are in direct contact with the flow path via the aforementioned openings so that the sample fluid to be analyzed contacts and flows around the protruding tip. In preferred embodiments, the tip protrudes about 25 to 50% into the flow path. In the embodiment shown in the Figures accompanying this application, the flow path makes one jog to an opening which, when the sensing module is assembled to the reference electrode, communicates with the reference electrode. However, it will be readily apparent to the skilled artisan that the flow path can be configured substantially straight.

The novel electrodes of this invention comprise an ion selective membrane material and at least one member for proper positioning of the electrode within a holder in the sensing module. The electrodes in a preferred embodiment, are devoid of external cables and connector, making contact with an analyzer via contact members resiliently mounted on the analyzer.

In one embodiment, an O-ring on the electrode centers and holds the electrode inside the measuring block until assembled to the mounting bracket and circuit board. When assembled, electrical spring contacts on the circuit board provide electrical contact and sealing force. The O-ring also provides a back up seal in the event the seal provided by the tip of the electrode fails.

In preferred embodiments, electrodes are fabricated in one piece, preferably molded, with a cylindrical body terminating in a spherical sensing tip at one end and at the opposite end in a contact member adapted to make electrical connection with a receiver for electrical signals, e.g., a signal processing board. The electrode provides electrical contact and contains one or more electrolyte fill solutions. This basic assembly is common to all electrodes in accordance with the present invention. Components of the electrodes, such as internal reference probes, fill solutions and ionic membrane material, acceptable for use in the present invention include those conventional in the art. Electrodes useful in the practice of this invention include sodium, potassium, chloride, lithium, calcium magnesium pH and others.

One particularly preferred sensing electrode for use in measuring the activity of ions in a fluid sample in this invention comprises:

(i) a hollow cylindrical body member;

(ii) a contact member disposed at one end of the body member, wherein the contact member is adapted to make electrical connection with a resiliently mounted electrical contact for receiving electrical signals from the electrode;

(iii) a hemispherical sensing tip disposed at one end of the body member, wherein the sensing tip is provided with an opening configured to align with and fit within an opening in a holder for the electrode when the electrode is placed therein, the opening in the holder being in communication with a flow path for the sample;

(iv) an ion selective membrane material disposed on the sensing tip, thereby sealing the opening therein and being capable of providing sealing contact with the opening in the electrode holder when the electrode is disposed therein;

(v) an internal reference electrode disposed in the body member and in electrical contact with the sensing tip and the contact member; and (vi) at least one positioning member disposed on the body member for positioning the electrode in the electrode holder.

In preferred embodiments, the ion selective membrane material also performs the function of sealing the opening in the flow path when the electrodes are disposed in the sensing module and the contact member of the electrode is engaged with a resiliently mounted electrical contact which pushes the sensing tip into sealing relation with the opening in the flow path.

The material of the ion selective membrane depends upon the particular ion to be measured as is well known to the skilled artisan.

Ion selective membranes useful in the practice of the present invention are capable of forming a seal with the opening between the flow path and the electrode holder. Such membranes are commercially available and are well known to the skilled artisan. These membranes include polymeric membranes, such as polyvinyl chloride (PVC) based membranes, readily available commercially.

The membrane material may be bonded to the exterior surface of the sensing tip, e.g., by use of an appropriate adhesive. One such method is described hereinafter.

The present invention also provides an electrode assembly for use in measuring the activity of ions in a fluid sample, wherein the assembly comprises at least one electrode holder and at least one sensing electrode, wherein the electrode holder comprises:

a hollow cylindrical member adapted to receive the sensing electrode and terminating at one end in a hemispherical sensing tip having an opening in communication with a flow path for the sample and at the opposite end in an opening to receive the electrode.

wherein the sensing electrode comprises an electrode as described above.

In preferred embodiments of the present invention the sensing module is provided with a plurality of such electrode assemblies to enable the measurement of a plurality of ions in the sample. The axis of the electrode holder, as well as the sensing electrode itself, is perpendicular to the flow path to enable sealing contact.

The area of the ion selective membrane material disposed directly over the opening in the tip of the electrode is the "active area" of the membrane. The "active area" of the membrane is dimensioned to fit with the opening between the flow path and electrode holder. In preferred embodiments, the active area of the membrane protrudes into the flow path so that it is sufficiently exposed to the fluid sample to enable measurement of the ion activity yet still enable a sufficient flow through the flow path. The appropriate degree of protrusion can be readily determined by the skilled artisan. Typically this protrusion does not exceed about 50% of the flow path.

In embodiments wherein the sensing module is provided with a plurality of electrodes it is preferred for ease of use to have a system which keys a particular electrode to a particular electrode holder and in a particular orientation. In one preferred embodiment, one or more pins disposed on the sensing module adjacent the opening of the electrode holder are designed to align with corresponding holes in an electrode, wherein the distribution of pins and holes are different for each electrode. These holes can be placed, e.g., on a rim surrounding the contact member. This insures proper identification of the electrode and proper mechanical location within the electrode holder and provides appropriate alignment of the active area of the ion selective membrane material and the opening between the flow path and the electrode holder. The rim is optionally provided with a finger access for removing the electrode from the holder.

To extend useful life, an evaporation barrier 40, e.g., a metalized label, shown in FIG.17, is optionally provided to cover the electrode body and minimize evaporative losses of electrolyte through the cylindrical body of the electrode. Metalized packaging such as aluminum foil with adhesive, metalized nylon film, and so forth are good candidates for extended shelf life.

In one embodiment wherein a sodium electrode is included in the sensing module, a membrane type neutral carrier sodium electrode is preferably used rather than the common glass electrode to preclude the daily etching required for the glass and possible upsetting of the chloride electrode, and to prolong calibration. It also simplifies the fluidics of the sensing module since cleaning of the glass electrode is eliminated.

In one preferred embodiment, the reference electrode component of the measuring block comprises a reservoir containing rechargeable KCl, a permeable membrane which is in electrical liquid contact with the flow path of the sensing module when these components are removably engaged, and a removable internal reference electrode.

In one preferred embodiment of the present invention, the closed reference electrode is provided with a large reservoir for extended life, and is also rechargeable thereby reducing frequency of replacement. In another preferred embodiment, the reference electrode is provided with a removable calomel assembly, junction and membrane. Recharging requires that the user remove, for example, the calomel section, add fresh electrode solution and KCl tablets, and reinstall the calomel section. A radial O-ring can be used to insure a leaktight seal which is not sensitive to applied force.

The appropriate reference electrode will depend upon the particular ions being measured and can be readily selected by the skilled artisan. In embodiments wherein the electrolyte is a KCl solution, the ion permeable membrane material is assembled to the reference electrode by means of concentric O-rings to seal from KCl leakage.

The liquid junction between the flow path of the sensing module and the ion permeable membrane of the reference electrode is readily formed in a preferred embodiment, by removably clamping the sensing module and the reference electrode.

The electrodes, sensing module and measuring block of the present invention are made from conventional materials known to the skilled artisan. To insure ease of manufacture of these components, it is advantageous to use a readily processable plastic such as nylon, PVC, acrylics and so forth where suitable. For components which are preferably transparent, transparent polyurethanes and polyolefins are useful.

The present invention also provides fluid systems which in a preferred embodiment comprise:

(i) an analyzer instrument containing electrical circuitry for analyzing the ion level of a sample and being adapted to receive a measuring block in accordance with this invention in such a manner to provide vertical disposition of the flow path and to provide electrical communication with the contact member of the sensing electrode via at least one resiliently mounted contact member;

(ii) a measuring block in accordance with this invention; and (iii) a pump for flowing sample to be analyzed downwardly through the flow path past the first opening in communication with the sensing electrode and the second opening in communication with the reference electrode.

One such preferred system of this invention embodies an open sample method wherein sample, calibrants and other reagents are deposited directly into a sample well comprising the inlet port in the sensing module and are aspirated through the flow path for analysis. Advantages of the open system include direct calibration, vertical orientation, simple fluidics and fast throughput. Other advantages of an open system include fewer ground loops, fast cycle, precise sample pickup and deposit, minimal clogging areas, and simple fluidic path. Furthermore, the fluidic analysis system of the present invention is flexible in that the sample and other reagents can be flowed uphill or downhill. One advantage of downhill flow path is that it enables a shorter flow path and, thus, smaller sample volume.

A downhill flow is particularly advantageous when the electrolyte in the reference electrode is a salt such as potassium chloride. Conventionally, the reference electrode is the last in the line of electrodes through which a sample passes to avoid contamination of the sensing electrode by the electrolyte of the reference electrode. Potassium chloride is a very useful electrolyte in reference electrodes. However, potassium chloride is very dense and, when the reference electrode is last in line in a fluid path which flows uphill, can fall back through the system flow path, past the lower sensing electrodes thereby contaminating them. Therefore, in such cases there is an advantage in having the reference electrode at the bottom of a flow path that flows downhill.

In some known systems, the sample and other liquids were flowed uphill because gravity helped remove the air bubbles. Air bubbles are not a significant factor in the present system because of and wash out of the path at high fluid flow velocities small, bubbles do not collect at critical measuring tips of the electrodes.

Reagents, such as calibrants are preferably stored in rigid plastic, e.g., high density polyethylene (HDPE) bottles.

BRIEF DESCRIPTION OF THE DRAWINGS

FIG. 8 is an enlarged partial view of the sensing module shown in FIG. 5 showing optical sensor, ground wire and contact thermal transducer and liquid junction between.

DETAILED DESCRIPTION OF THE INVENTION

The measuring blocks of the present invention are particularly useful in systems for analyzing the ion level of a fluid sample.

Figure 1:
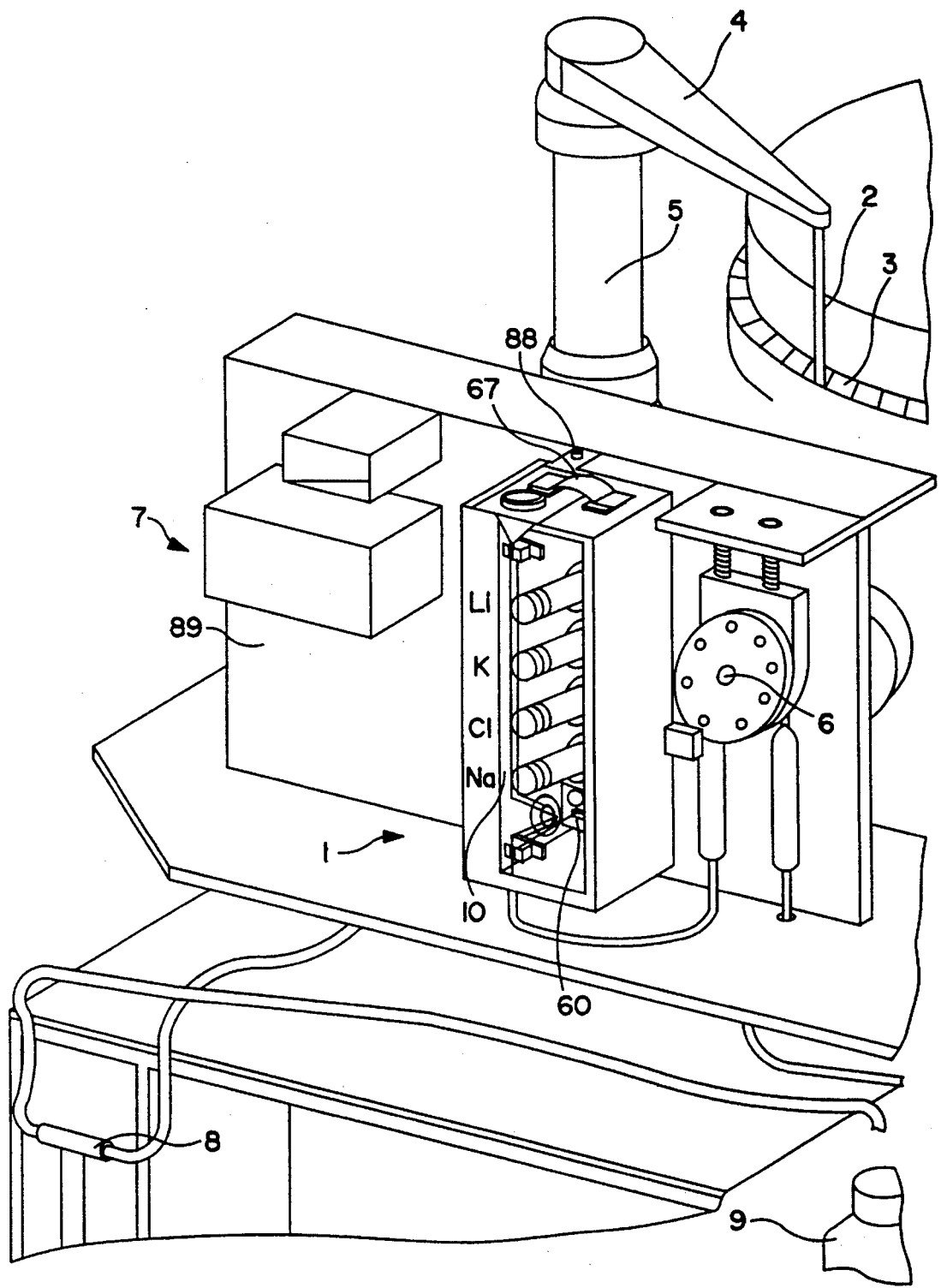
FIG. 1 is perspective view of one preferred measuring block of this invention, including portions of a preferred fluid analysis system.
Figure 2:
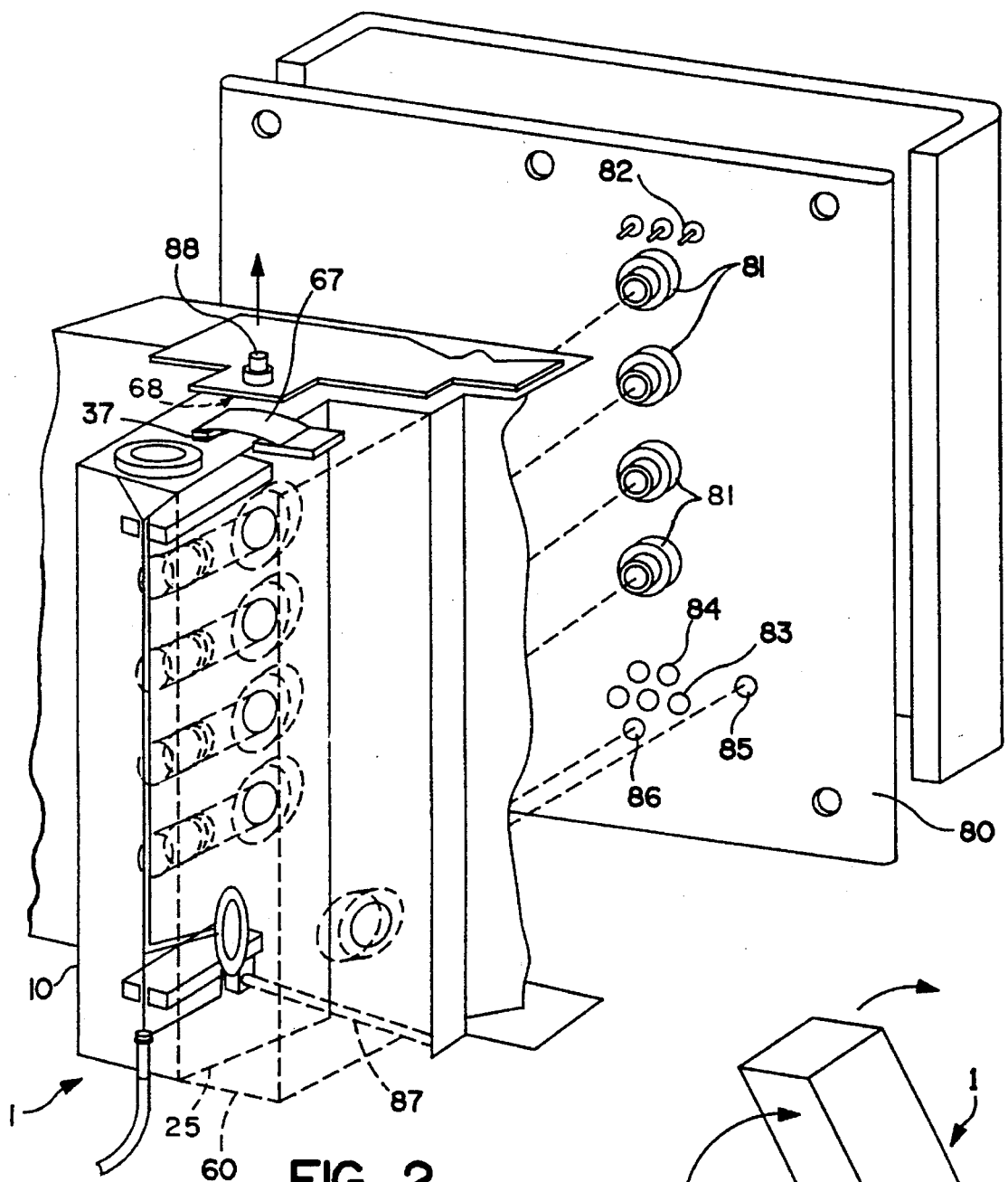
FIG. 2 is a cut-away perspective view showing the measuring block (sensing module and reference electrode) of FIG. 1 and signal processing board containing contacts for the sensing electrodes, temperature transducer and optical sensors of the measuring block.
Figure 3:
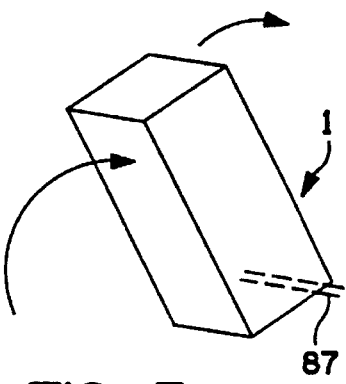
FIG. 3 is a diagram illustrating a preferred way in which the measuring block can be connected to the signal processing board.

In FIGS. 1, 2 and 3 one preferred measuring block of this invention is shown in conjunction with a portion of a preferred fluid analysis system which includes a conventional analyzer instrument containing electrical circuitry for analyzing the ion level of a fluid sample. In the embodiment shown in FIGS. 1, 2 and 3, measuring block 1 is adapted to mechanically contact to a receiving portion of the analyzer instrument, in this case, signal processing board 80 shown in detail in FIG. 2.

Figure 16:
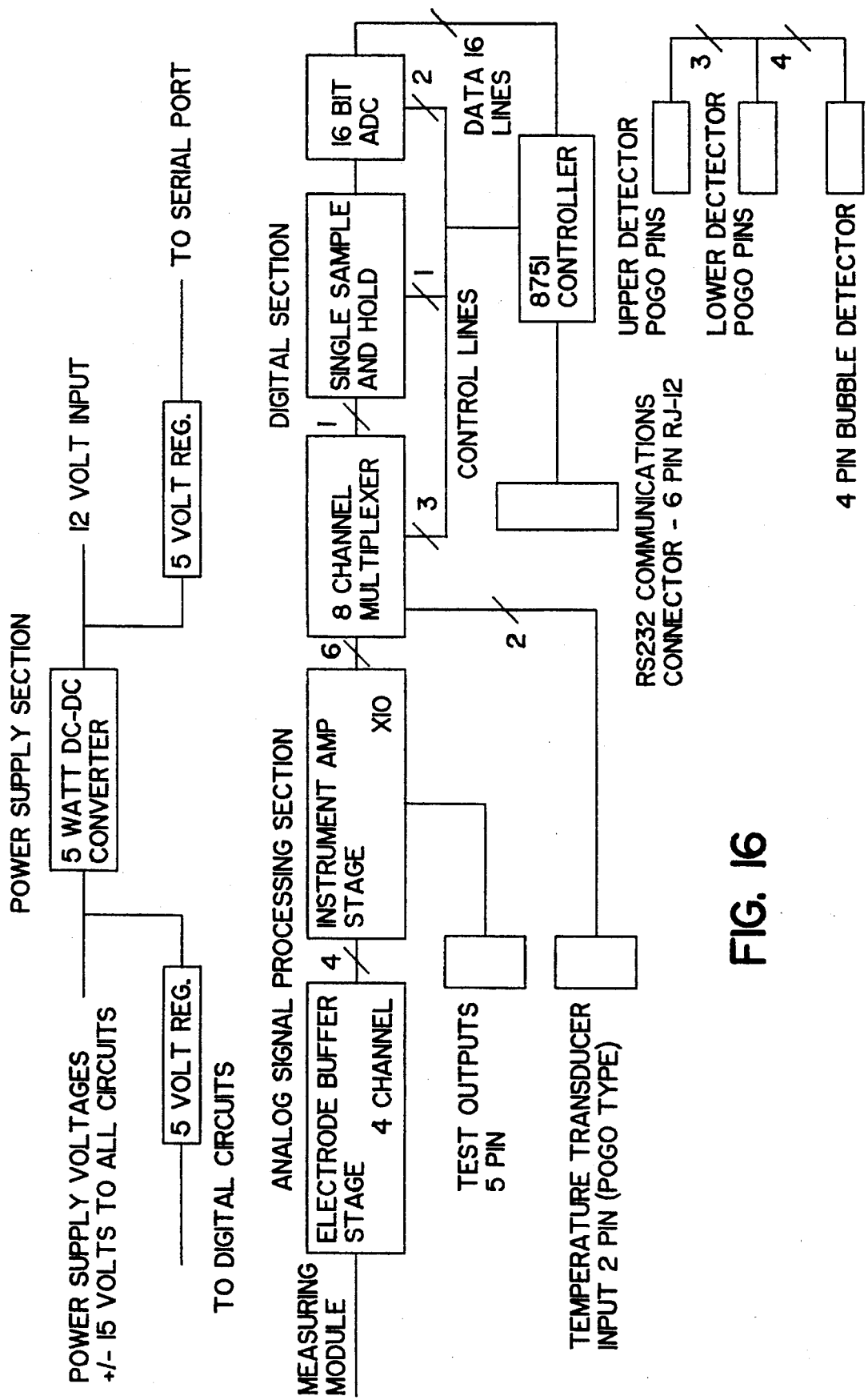
FIG. 16 is a block diagram of one signal processing board for use in the present invention.
Figure 17:
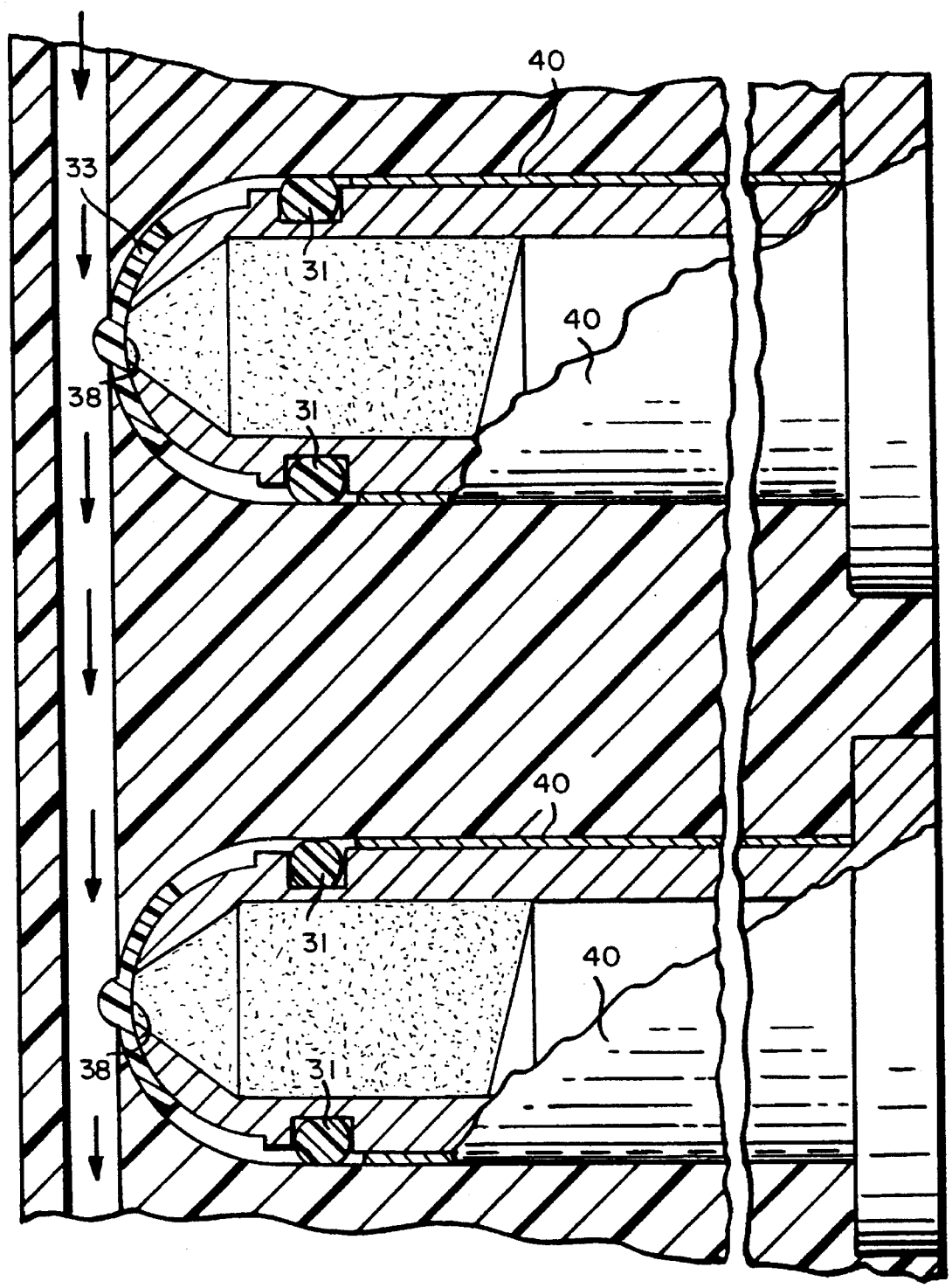
FIG. 17 is an enlarged side view and partial sectional view of the sensing module shown in FIG. 5.

In FIG. 1 measuring block 1 is shown assembled to signal processing board 80 which is provided with contacts for the various electrical components of measuring block 1. FIG. 16 shows a schematic of a conventional signal processing board which can be used in the practice of the present invention. As shown in FIG. 1, measuring block 1 comprises sensing module 10 and reference electrode 60 which are removably engaged by reference latch 67 and reference pin 85, shown in detail in FIG. 5. Measuring block 10 is mechanically engaged to the analyzer instrument by means of locking pin 88, locking pin slot 68 and pivot bar 87 shown in FIGS. 2, 3 and 4. Measuring block 1 is slid over bar 87 and pivoted towards spring loaded contacts (not shown).

Figure 15:
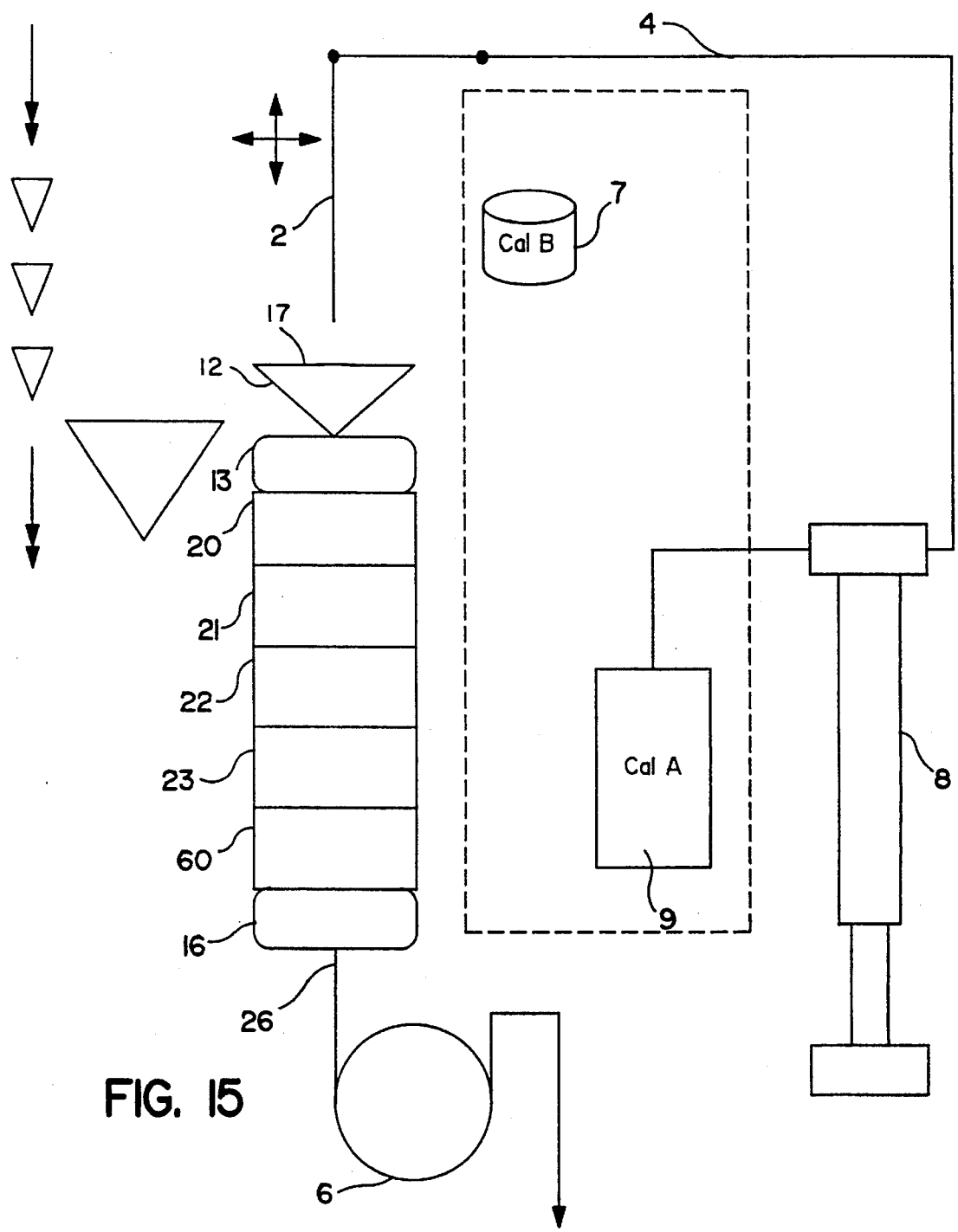
FIG. 15 is a schematic representation of a preferred fluid analysis system of the present invention.

Also shown in FIG. 1 is a liquid delivery system comprising sampler arm 4 and sample probe 2 by means of which sample, calibrants and other solutions can be introduced to measuring block 1. Although the invention will be described in conjunction with a preferred open liquid delivery system as shown in FIGS. 1 and 15, it will be readily apparent to the skilled artisan that any variety of fluid delivery systems can be used to deliver sample and other reagents to measuring block 1.

Measuring block 1 comprises sensing module 10 and reference electrode 60.

Sensing module 10 is shown in FIGS. 1, 2, 4 and 5. The optically clear sensing module 10 is provided with a plurality of holders in which are disposed sensing electrodes 20 to 23, provides optical windows for optical sensors 13,16 (bubble/position detectors), module temperature monitor 24 and open sample well 12, which can be provided with a partial cover to minimize splashing and aerosols. As shown, sensing module 10 is block shaped and constructed of transparent material so that the fluid flow can be observed by a user.

Figure 4:
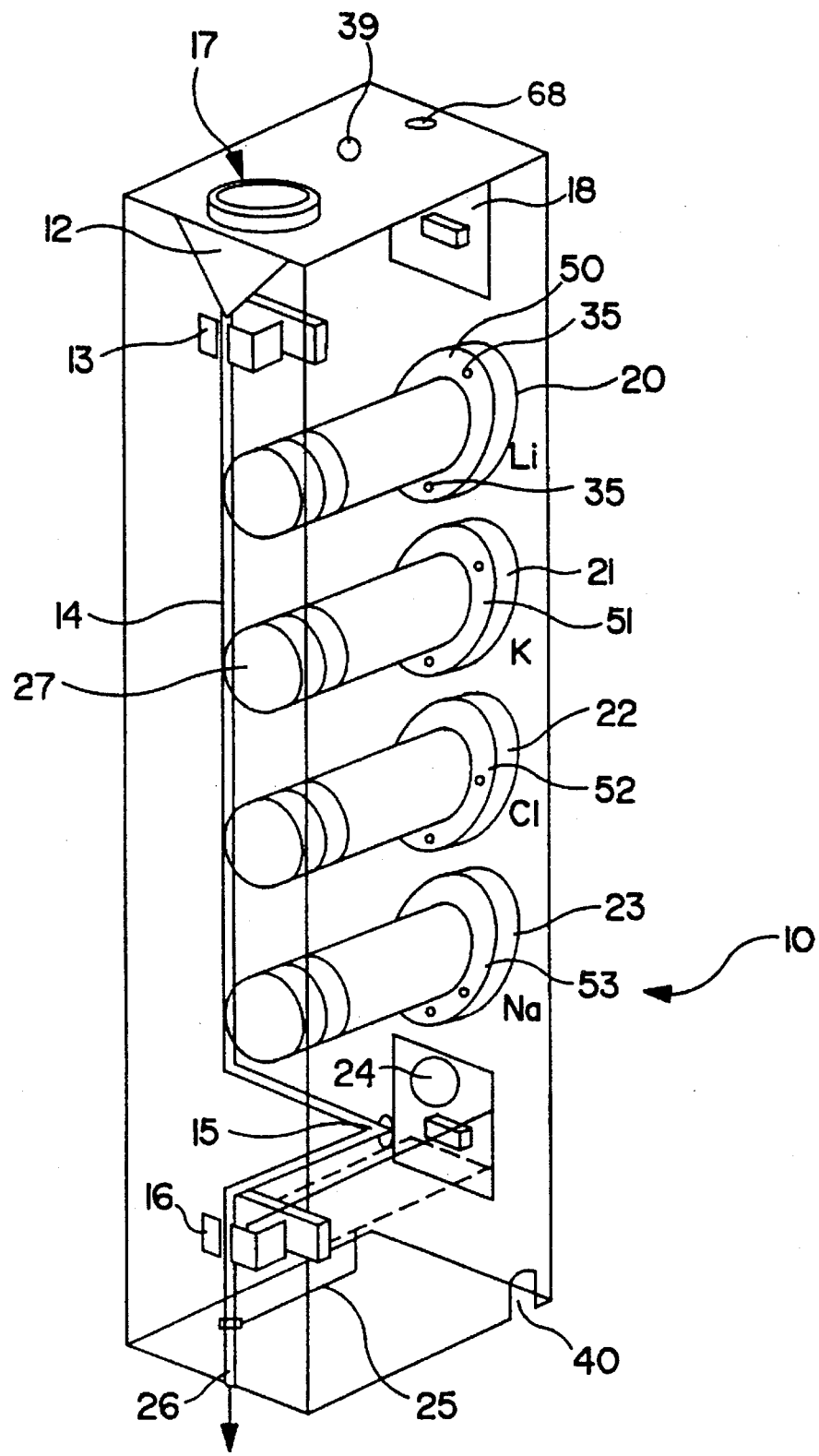
FIG. 4 is an enlarged perspective view of the sensing module shown in FIGS. 1 and 2.

Referring now to FIG. 4, sensing module 10 is provided with inlet port 17, outlet port 26, and flow path 14 which connects inlet port 17 and outlet port 26. Sensing module 10 is provided with a plurality electrode holders which are in communication with flow path 14 via openings 27 between flow path 14 and the electrode holders. As shown in the figures, electrodes 20, 21, 22 and 23 are disposed in the holders so that the tips of the electrodes are in communication with flow path 14 through openings 27.

Figure 8:
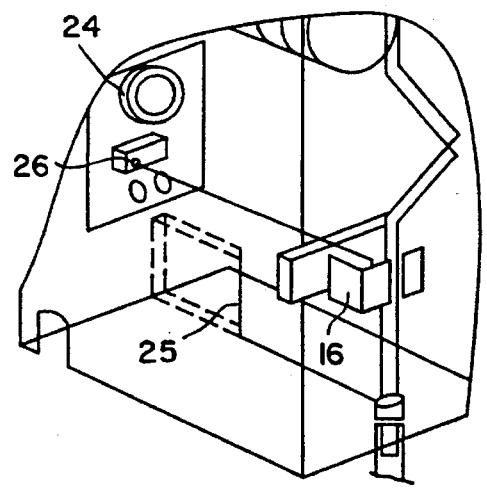
Figure 7:
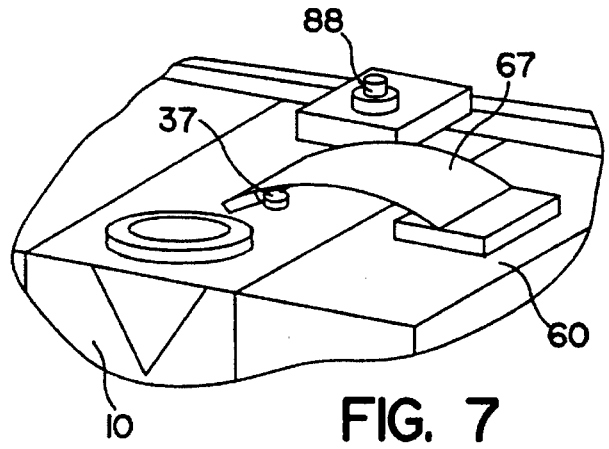
FIG. 7 is an enlarged partial view of the top section of the measuring block shown in FIGS. 1 and 2.

Sensing module 10 is optionally provided optical sensors. The embodiment shown in FIG. 2 is provided with an upper optical sensor 13 and a lower optical sensor 16 for determining, e.g., whether or not there is sample present in the flow path. FIG. 8 is an enlarged view of the lower section of sensing module 10 shown in FIG. 5. It shows lower optical sensor 16, ground contact 26, ground wire 25 and contact thermal transducer 24. When optical sensors 13 and 16 are present, optical sensor contact pin board 18 is used to provide the necessary electrical contact with the analyzer, through signal processing board 80 shown in FIG. 2. Reference numeral 86 (shown in FIG. 2) indicates the pin for receiving a ground contact, i.e., ground wire 25, disposed in module 10. When module 10 is installed on signal processing board 80, pin 86 connects with ground wire 25 disposed in module 10. Spring loaded pins 82 make contact with optical sensor 13. Pin 83 makes contact with lower optical sensor 16. Pin 84 is the contact for temperature transducer 24. Pin 85 is the contact for reference electrode 60.

In the embodiment shown, sensing module 10 is provided with latch locking pin 37 in order to provide a means for removably engaging sensing module 10 and reference electrode 60 through reference latch 67.

Sensing module 10 is provided with locking pin slot 68 shown in FIG. 4 to receive module locking pin 88 shown in FIG. 2, to mechanically engage measuring block 1 to the analyzer instrument.

Figure 9:
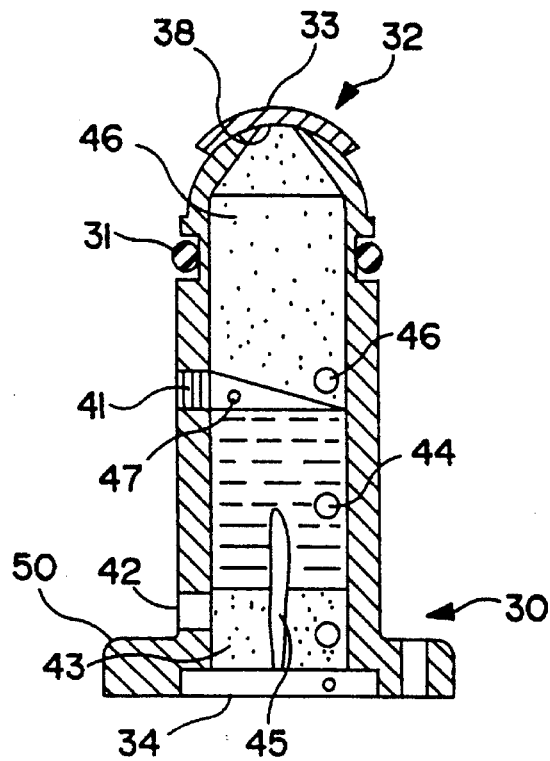
FIG. 9 is a cross-section through one sensing electrode in accordance with the present invention.
Figure 10:
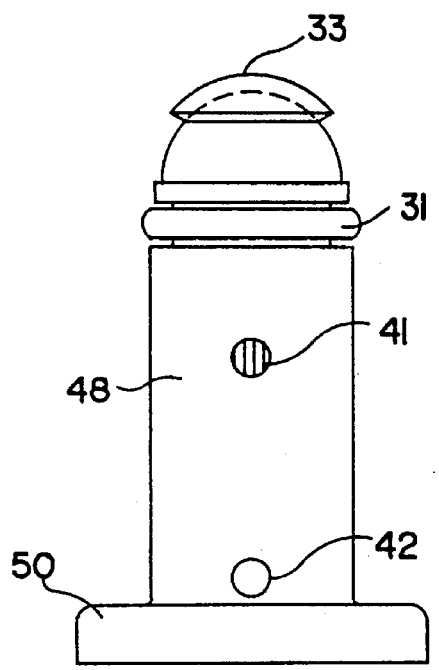
FIG. 10 is a schematic showing the outside of the electrode of FIG. 9.
Figure 11:
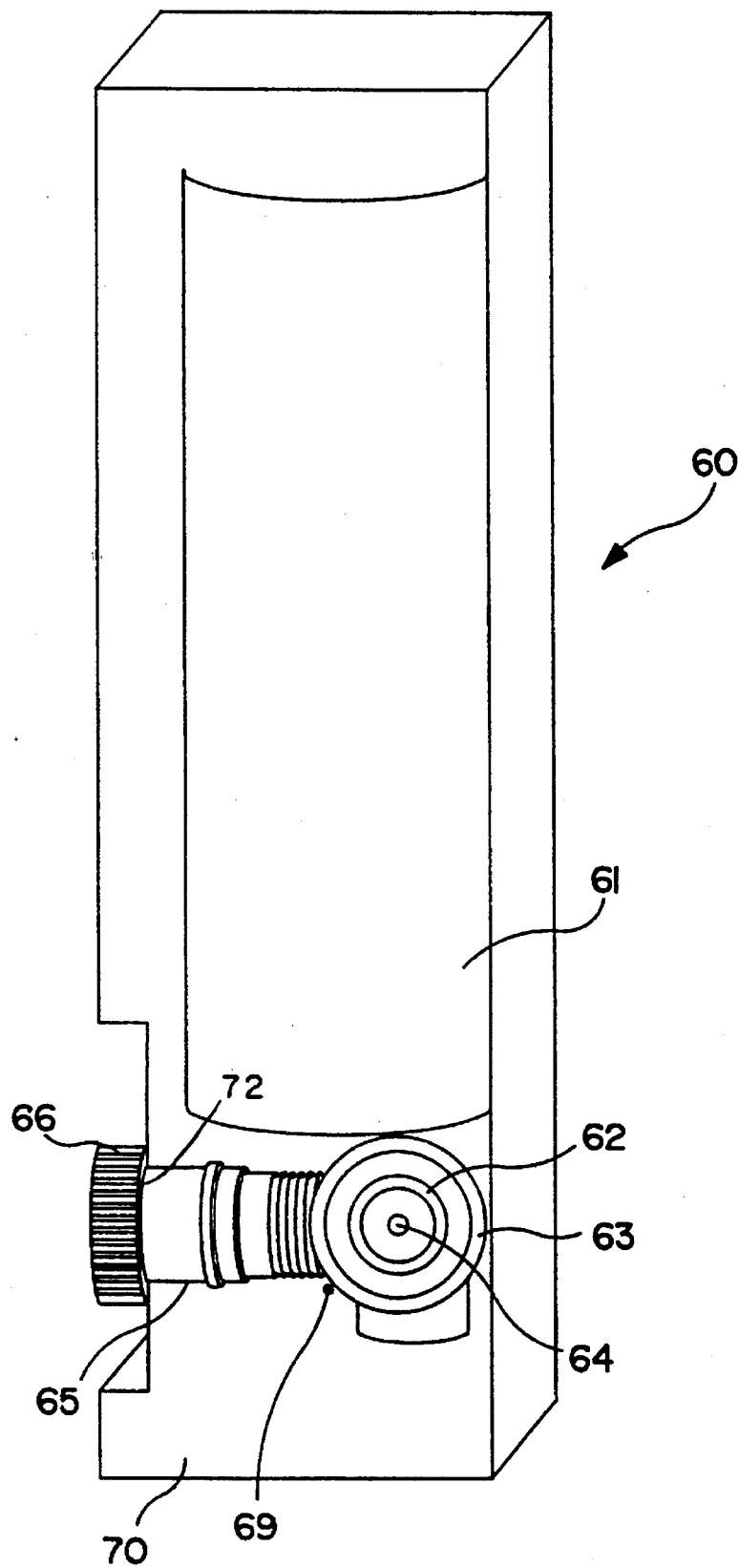
FIG. 11 is an enlarged perspective view of the reference electrode shown in FIGS. 1 and 2.
Figure 12:
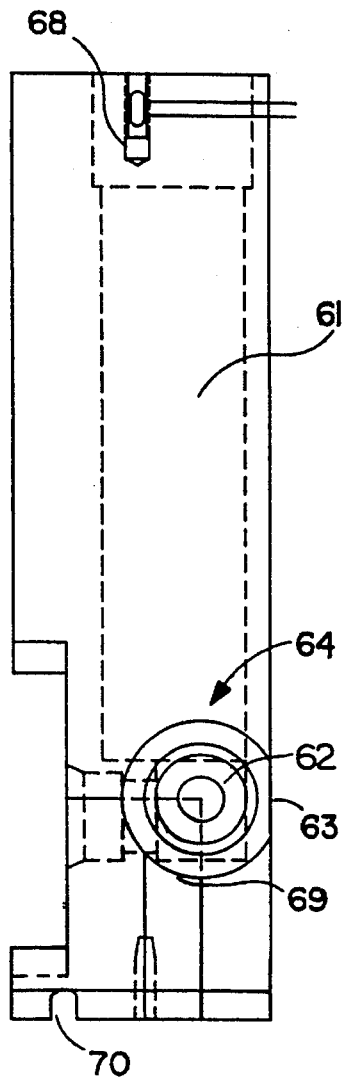
FIGS. 12, 13 and 14 are sections through the reference electrode shown in FIG. 11.
Figure 13:
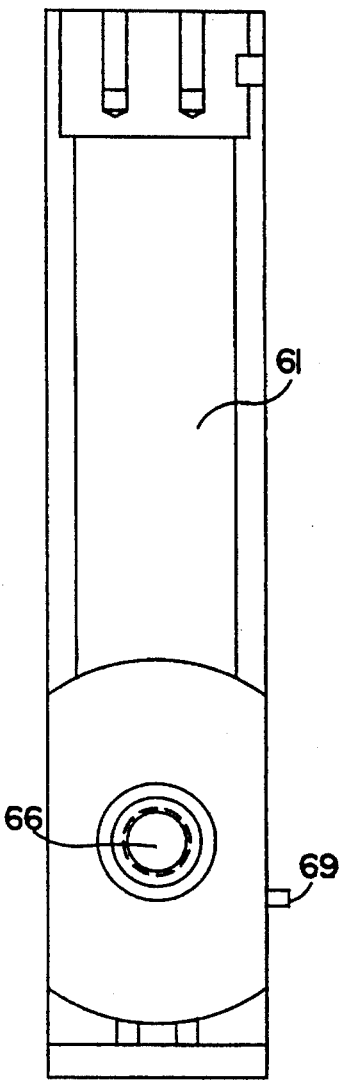
Figure 14:
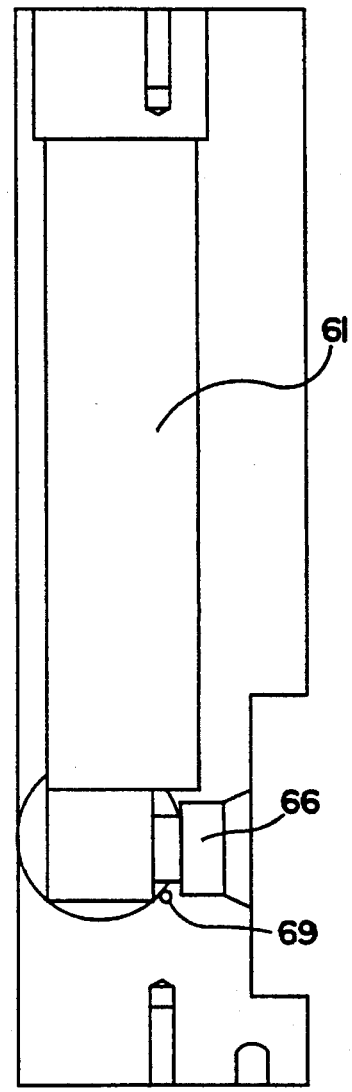

The novel electrodes of the present invention are shown in FIGS. 1, 2, 4, 5 and 6, and cross-section views in FIGS. 9 and 10. A representative electrode 30 is shown in FIGS. 9 and 10. The electrode comprises a cylindrical body member 48 terminating in spherical sensing tip 32 at one end and at the opposite end in contact member 34 and rim 50. Sensing tip 32 is provided with opening 38 over which is sealably disposed ion selective membrane material 33. Opening 38 and the section of membrane directly covering the opening, together, comprise the active section of the membrane. The active section of the membrane is dimensioned to fit within opening 27 in flow path 14 as shown in FIG. 4. It is preferred that the active area of the electrode be within opening 27 in order to minimize electrode drift.

Ion selective membrane material 33 is compliant to provide sealable contact with opening 27 between flow path 14 and the electrode holder. O-ring 31 positioned on the outer surface of cylindrical body member 48, near sensing tip 32, positions the electrode inside the electrode holder until assembled to signal processing board 80 as shown in FIG. 2. Spring loaded contact members 81 shown in FIG. 2, make electrical contact with contact member 34 shown in FIGS. 6 and 9 when measuring block 1 is assembled to signal processing board 80 as shown in FIG. 2. Spring loaded contacts 81 on signal processing board 80 also provide sealing force to seal ion selective membrane material 33 against opening 27. In the embodiment shown in FIGS. 6 and 9, contact member 34 comprises a gold plated pc board to make spring contact via POGO™ pins 81 to the signal processing board 80 shown in FIG. 2.

It is important that the axis of cylindrical body member 48 be perpendicular to the axis of flow path 14 to insure sealing of openings 27 by ion selective material 33. O-ring 31 centers electrode 30 and also provides a backup seal should the seal provided by ion selective membrane material 33 fail.

In the embodiment shown in FIG. 10 the electrode is provided with two fill holes 41, 42. Epoxy 43 is injected through fill hole 42 and cured to cement contact member 34 in place and to seal the electrode. Secondary fill hole 41 is first used to inject a layer of gelatin 44 which serves to protect probe 45 from air bubbles which could de-stabilize the voltage and cause electrode drift. Once gelatin 44 is in place secondary fill hole 41 is used to provide electrolyte 46 to the electrode. In the embodiment shown air bubble 47 remains inside the electrode (about 1 to 10 μl, preferably about 5 μl). Air bubble 47 serves to take up compression as liquid expands with temperature changes inside the electrode. Without something to take up the compression it is possible to deform or rupture ion sensitive membrane material 33. Secondary fill hole 41 may be filled with, for example, wax, to seal it.

Figure 5:
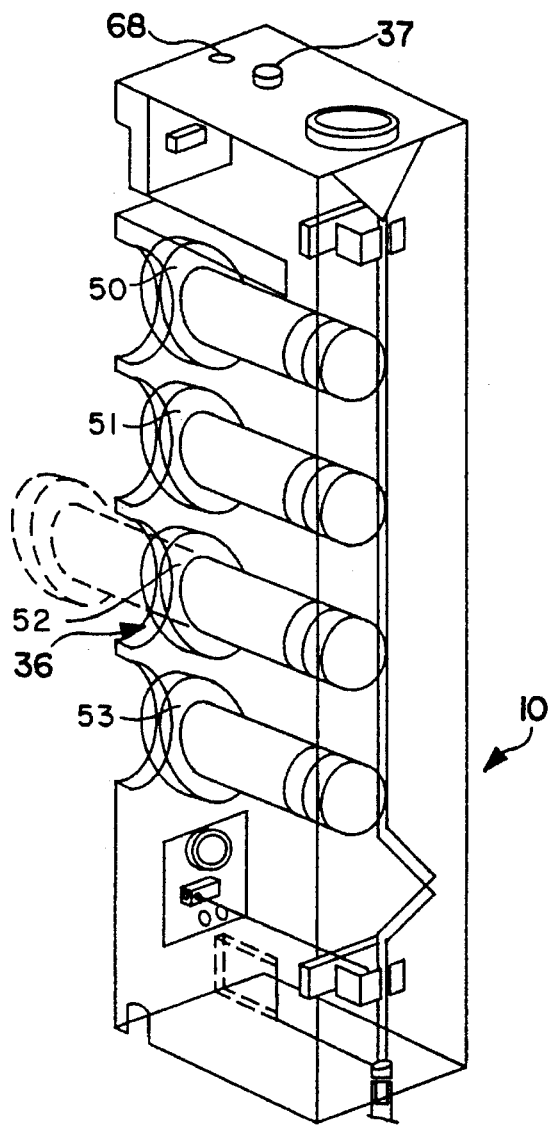
FIG. 5 is similar to FIG. 4 and shows finger accesses for removing sensing electrodes.
Figure 6:
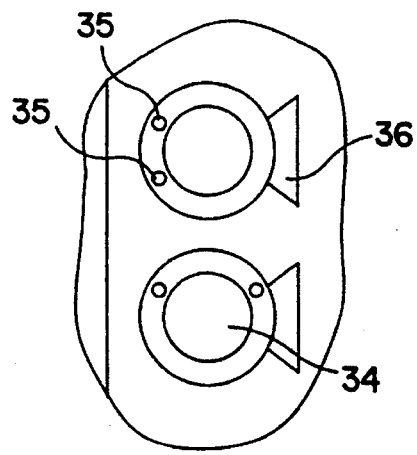
FIG. 6 is an enlarged rear view of two electrodes disposed in the sensing module of FIG. 5.

Rim 50, 51, 52, 53 shown in FIGS. 4 and 5 provides finger access via finger access 36 shown in FIG. 5 and position key hole 35.

Ion selective membrane material 33 was sealed to the tip of an electrode of the present invention as follows. Ion selective membrane material was sized and placed in a hemispherically concave portion of a teflon block, wherein the concave portion was dimensioned to receive the spherical tip of an electrode. A teflon rod was disposed in the electrode and through opening 38 in the spherical tip of the electrode and glue was then applied to the tip. The teflon rod which protruded through opening 38 was placed in the center of the membrane material disposed in the teflon block. The electrode was then moved down the teflon rod to contact with and adhere to the membrane material. This method kept the active portion of the membrane essentially glue-free.

Reference electrode 60 shown in FIGS. 1, 2 and 11–14 is provided with reference latch 67 shown in FIGS. 1 and 2 which engages locking pin 88 of sensing module 10 for removable engagement with sensing module 10 to form measuring block 1. The surface of reference electrode 60 which contacts sensing module 10 (shown in FIG. 11) is provided with pin 69 which engages a reciprocal locking pin slot (not shown) on sensing module 10. When sensing module 10 and reference electrode 60 are engaged through locking pins and reciprocal locking pin slots, the module reference latch 67 present on the top of reference electrode 60, is engaged with locking pin 88 on sensing module 10. A similar latch locking pin and module reference latch are present on the bottom of the sensing module and reference electrode to provide movably sealable contact between the two members. These are not shown in the drawings.

Reference electrode 60 comprises a tablet reservoir 61 for receiving fill solution. The electrode is filled through the opening over which permeable reference membrane 64 is placed or alternatively through the opening 72 in reference electrode 60 which receives calomel insert 66. O-ring 65 provides a seal.

Reference electrode 60 is provided with pivot slot 70 which, when sensing module 10 and reference electrode 60 are removably engaged to form measuring block 1, aligns with pivot slot 40 in sensing module 10.

Reference electrode 60 is provided with reference membrane 64 which is sealably disposed therein by means of concentric O-rings 62, 63.

The fluid analysis system of the present invention is partially shown in FIG. 1 and is schematically illustrated in FIG. 15. The measuring block shown schematically in FIG. 15 is provided with upper and lower optical sensors as well as lithium, potassium, chlorine, and sodium electrodes. It will be readily appreciated by the skilled artisan that the optical sensors are optional as is the selection of electrodes used in the measuring block.

The fluid analysis system of the present invention is simplified in that it embodies only one peristaltic pump 6 and a syringe pump 8. The system provides for the use of two calibrants, calibrant A and calibrant B. The system of the present invention is valveless, except for a valve in the syringe pump.

No valves are required for calibration. Calibrants are deposited directly into inlet port 17 of measuring block 10.

Calibrant A is refreshed by syringe pump 8 and stored in a bottle 9 connected thereto. Calibrant B is aspirated from an open bottle 7. The direct aspiration method of the fluid analysis system of the present invention is very desirable for simplicity, high reliability and high throughput.

Sample probe 2, e.g., a syringe, picks up sample, e.g., from cuvette carousel 3, calibrant B, and deproteinizer from station points on sampler arm path and dispenses into the inlet port 17 of measuring block 1. Calibrant A is delivered directly from syringe pump 8 through sample probe 2. Syringe pump 8 is preferably selected over a peristaltic pump to minimize maintenance, increase flow rate, response time and improve accuracy and precision of aspirated and dispensed volumes.

Peristaltic pump 6 directly aspirates sample, and other fluids through the measuring block from inlet port 12. In the embodiment shown, peristaltic pump 6 is used in conjunction with the optical sensors 13, 16 for sample positioning within measuring block 1. Pump 6 is also used in conjunction with syringe pump 8 to aspirate through slugs of calibrant A and air to clean flow path 14.

Optical sensors 13, 16 are preferably used in the measuring block to verify sample. The bottom sensor 16 is used to change speed of aspiration pump 6 for various fluidic functions during a measuring cycle and the top sensor 13 is used to check for "air in the sample" detection when a sample reading occurs.

This invention will be further understood with reference to the following example which is purely exemplary in nature and is not meant to limit the scope of the invention.

EXAMPLE

A fluid analysis system substantially similar to that in the figures was constructed. Reagents were stored in rigid HDPE bottles.

The measuring block consisted of four basic components.

(a) Removable sensing module 10 with electrodes 20–23, optical sensors 13,16, sample well 17 and temperature detector 24.

(b) Removable reference electrode 60 with rechargeable KCl reservoir 61.

(c) Signal processing, communications and connector board 80.

(d) Mounting bracket 89 with integrated peristaltic pump 6, calibrant B bottle holder 7 and wash station 5.

The overall size of the module envelope with mounting bracket (approximately):

6.5" high×11" wide×4" deep (clearance is provided with the sampler arm within the envelope)

The optically clear sensing module 10 houses the measuring electrodes 20–23, provides optical windows for the bubble/position detectors 13,16, module temperature monitor 24 and an open sample well with a partial cover to minimize splashing and aerosols. To minimize clogging and bubble traps, the sample path from inlet to outlet is straight, except a jog to reference junction 15, with no seals other than that provided by the sensing tips of the electrodes. Sensing tip 32 intersects the 0.050" diameter flow path by approximately 50% (0.025"). Opening 27 between flow path 14 and the electrode holder is sealed by the compliant membrane material 33 in direct contact with the flow path. A sample well is machined into the cuvette and holds 425 uL (sample size=280 uL) to prevent an overflow condition. Optical ports are located in the flow path below the sample well and after reference junction 15. The electrodes 20 to 23 are stacked in line on one side for ease of replacement and electrical contact with the circuit board. An O-ring 31 on the electrode body 48 centers and holds the electrode inside the measuring module until assembled to the mounting bracket and circuit board. Electrical spring contacts on the circuit board provide electrical contact and sealing force for the sensing tip.

The reference electrode 60 with removable calomel assembly 66, junction 15 and membrane 64 is combined with a large (90 day minimum) reference solution reservoir 61 and can be considered as a rechargeable device. Initially, the electrode can be charged (KCl tablets) at the factory and membrane 64 added when assembled to the measuring block. Subsequent recharging requires that the user remove the calomel section 66, add fresh solution and tablets, and reinstall the calomel section. A radial O-ring 65 insured a leaktight seal and was not sensitive to applied force.

The board 80 was approximately 6.0"×7.5" and contained the front end analog amplifiers, a 16 bit A/D converter, a RS232 serial communication port and a DC-DC converter for the required ±15 & 5 volts. Connectors were provided for the serial interface, power input, chart recorder output, buffer amplifier output, via RS232 only and bubble detector output. A block diagram is shown in FIG. 16.

The mounting plate 89 divides the fluidic and electronic sides, provides means to mount ISE related components, provides electrical and liquid shielding, and mounts to the analyzer mounting plate. The mounting plate is accessible from the top or front and allows components to be readily removed.

It is understood that the example and embodiments described herein are for illustrative purposes only and that various modifications or changes in light thereof that will be suggested to persons skilled in the art are to be included within the spirit and purview of this application and the scope of the approved claims.

What is claimed is:

1. An electrode assembly for use in measuring the activity of ions in a fluid sample, the assembly comprising at least one electrode holder and at least one sensing electrode, wherein the electrode holder comprises:

a hollow cylindrical holding member adapted to receive the sensing electrode, the hollow cylindrical holding member terminating at one end in a hemispherical section having an opening in communication with a flow path for the sample and at the opposite end in an opening to receive the electrode;

wherein the electrode comprises:

(i) a cylindrical body member;

(ii) a contact member disposed at one end of the body member, wherein the contact member is adapted to make electrical connection with a resiliently mounted electrical contact for receiving electrical signals from the electrode when the sensing electrode is disposed in the electrode holder;

(iii) a hemispherical sensing tip disposed at one end of the cylindrical body member, wherein the sensing tip is provided with an opening configured to align with and fit within the opening in the hemispherical section of the electrode holder when the electrode is placed therein;

(iv) a compliant ion selective membrane material bonded on the outer surface of the hemispherical sensing tip and sealing the opening therein and, when the electrode is disposed in the holder, simultaneously (a) providing sealing contact with the opening between the flow path and the electrode holder, and (b) protruding into the flow path to provide contact with the sample;

(v) an internal reference electrode disposed in the body member and in electrical contact with the sensing tip and the contact member; and (vi) at least one positioning member disposed on the body member for positioning the electrode in the electrode holder.

2. An electrode assembly in accordance with claim 1, wherein the sensing electrode further comprises an evaporation barrier.

3. An electrode assembly in accordance with claim 2, wherein the evaporation barrier comprises a metalized material.

4. An electrode assembly in accordance with claim 1, wherein one sensing electrode is a membrane type neutral carrier sodium electrode.

5. An electrode assembly in accordance with claim 1, wherein the hemispherical sensing tip protrudes into the flow path up to about 50%.

6. An electrode assembly in accordance with claim 5, wherein the hemispherical sensing tip protrudes into the flow path from about 25% to about 50%.

7. An electrode assembly in accordance with claim 1, wherein the contact member of the sensing electrode is provided with a rim member.

8. An electrode assembly in accordance with claim 7, wherein the rim member has one or more position key holes disposed therein.

9. An electrode assembly in accordance with claim 7, wherein the rim member is provided with at least one finger access.

10. A sensing module for use in measuring the ion activity of a fluid sample, wherein the sensing module comprises:

(i) a flow-through cell having at least one inlet port and at least one outlet port;

(ii) at least one flow path in the cell for the sample, the flow path being in communication with the inlet and outlet ports and having at least two openings between the ports, a first opening for communicating with a sensing electrode and a second opening for communicating with a reference electrode;

(iii) at least one hollow cylindrical holding member in the cell adapted to receive the sensing electrode and terminating at one end in a hemispherical section which is provided with a first opening in communication with the flow path for the sample and at the opposite end in a second opening to receive the sensing electrode; and (iv) at least one sensing electrode, wherein the sensing electrode is disposed in the hollow cylindrical holding member and comprises:

(a) a hollow cylindrical body member;

(b) a contact member disposed at one end of the body member, wherein the contact member is adapted to make electrical connection with a resiliently mounted electrical contact for receiving electrical signals from the electrode;

(c) a hemispherical sensing tip disposed at one end of the cylindrical body member, wherein the sensing tip is provided with an opening configured to align with and fit within the first opening in the hemispherical section of the electrode holder when the electrode is received therein through the second opening;

(d) a compliant ion selective membrane material bonded on the outer surface of the hemispherical sensing tip, thereby sealing the opening therein and simultaneously 1) providing sealing contact with the opening between the flow path and the electrode holder, and 2) protruding into the flow path to provide contact with the sample;

(e) an internal reference electrode disposed in the body member and in electrical contact with the sensing tip and the contact member; and (f) at least one positioning member disposed on the body member for positioning the electrode in the electrode in the electrode holder.

11. A sensing module in accordance with claim 10, wherein the flow-through cell comprises a transparent plastic.

12. A sensing module in accordance with claim 10, wherein the flow path from the inlet port past the sensing electrodes is substantially straight.

13. A measuring block for use in measuring the ionic activity of a fluid sample, wherein the measuring block is removably engageable to an analyzer instrument containing electrical circuitry for receiving electronic signals from an electrode in the measuring block and, wherein the measuring block comprises:

a sensing module in accordance with claim 12 and a reference electrode removably engaged thereto, wherein the reference electrode comprises:

(i) a body member, adapted to be removably engageable to the sensing module, the body member having, an opening which is sealed by an ion permeable membrane material and is in communication with the second opening of the flow path.

14. A measuring block in accordance with claim 13, wherein the measuring block is adapted for removable attachment to an analyzer instrument to provide electrical communication between the sensing and reference electrodes and the analyzer.

15. A fluid analysis system comprising:

(i) an analyzer instrument containing electrical circuitry for analyzing the ion level of a sample and being adapted to receive a measuring block;

(ii) a measuring block in accordance with claim 14 in electrical communication with the analyzer instrument in such a manner to provide vertical disposition of the flow path and to provide electrical communication with the contact member of the sensing electrode via at least one resiliently mounted contact member; and (iii) a pump for flowing sample to be analyzed downwardly through the flow path past the first opening in communication with the sensing electrode and the second opening in communication with the reference electrode.

16. A sensing module in accordance with claim 10, wherein the sensing module is adapted for removable attachment to a reference electrode to provide electrical liquid communication between the flow path and reference electrode.

17. A sensing module in accordance with claim 10, comprising a plurality of sensing electrodes.

* * * * *